US009689873B2

(12) United States Patent
Chaumat (10) Patent No.: US 9,689,873 B2
(45) Date of Patent: Jun. 27, 2017

(54) METHOD FOR DIAGNOSING AND DIFFERENTIATING HIV-2 INFECTIONS

(71) Applicant: BIO-RAD INNOVATIONS, Marnes la Coquette (FR)

(72) Inventor: Pierre Chaumat, Les Clayes sous Bois (FR)

(73) Assignee: BIO-RAD INNOVATIONS, Marnes la Coquette (FR)

( * ) Notice: Subject to any disclaimer, the term of this patent is extended or adjusted under 35 U.S.C. 154(b) by 0 days.

(21) Appl. No.: 14/403,618

(22) PCT Filed: May 30, 2013

(86) PCT No.: PCT/EP2013/061175
§ 371 (c)(1),
(2) Date: Nov. 25, 2014

(87) PCT Pub. No.: WO2013/178737
PCT Pub. Date: Dec. 5, 2013

(65) Prior Publication Data
US 2015/0168406 A1 Jun. 18, 2015

(30) Foreign Application Priority Data

May 30, 2012 (EP) .................................. 12305596

(51) Int. Cl.
| C12Q 1/70 | (2006.01) |
| G01N 33/569 | (2006.01) |
| G06F 19/00 | (2011.01) |

(52) U.S. Cl.
CPC ..... *G01N 33/56988* (2013.01); *G06F 19/345* (2013.01); *G01N 2333/162* (2013.01); *G01N 2458/00* (2013.01); *G01N 2469/20* (2013.01)

(58) Field of Classification Search
None
See application file for complete search history.

(56) References Cited

U.S. PATENT DOCUMENTS

| 5,721,095 A | 2/1998 | Chan et al. |
| 5,859,193 A | 1/1999 | Devare et al. |

(Continued)

FOREIGN PATENT DOCUMENTS

| JP | H5-507559 | 10/1993 |
| JP | H11-313671 | 11/1999 |

(Continued)

OTHER PUBLICATIONS

Sweep et al. "Analytical Aspects of Biomarker Immunoassays in Cancer Research" in Cancer Drug Discovery and Development: Biomarkers in Breast Cancer: Molecular Diagnostics for Predicting and Monitoring Therapeutic Effect Edited by: G. Gasparini and D. F. Hayes © Humana Press Inc., Totowa, NJ. 2006: pp. 17-30.*

(Continued)

*Primary Examiner* — Janet L Andres
*Assistant Examiner* — Stuart W Snyder
(74) *Attorney, Agent, or Firm* — Saliwanchik, Lloyd & Eisenschenk (57) ABSTRACT

The present invention provides a method using immunoassay devices to differentiate infection with HIV-2 from infection with both HIV-1 and HIV-2 in a subject.

26 Claims, 5 Drawing Sheets

(56) References Cited

U.S. PATENT DOCUMENTS

| 6,153,377 | A | 11/2000 | Devare et al. |
| 6,538,127 | B1 | 3/2003 | Devare et al. |
| 2001/0023076 | A1 | 9/2001 | Guan et al. |
| 2010/0120061 | A1* | 5/2010 | Badwan ............... G01N 33/558 435/7.2 |

FOREIGN PATENT DOCUMENTS

| JP | 2008-533472 | | 8/2008 | |
| JP | 2009-506319 | | 2/2009 | |
| WO | WO 91/19011 | | 12/1991 | |
| WO | WO 95/23973 | | 9/1995 | |
| WO | WO 2006/098804 | | 9/2006 | |
| WO | WO 2006/099191 | | 9/2006 | |
| WO | WO 2007/024633 | | 3/2007 | |
| WO | WO 2007/084021 | * | 7/2007 | ....... G01N 33/56988 |

OTHER PUBLICATIONS

De Cock et al. Rapid and specific diagnosis of HIV-1 and HIV-2 infections: an evaluation of testing strategies. AIDS.1990; 4(9):875-878.*

Andersson et al. Field evaluation of alternative testing strategies for diagnosis and differentiation of HIV-1 and HIV-2 infections in an HIV-1 and HIV-2-prevalent area. AIDS. 1997; 11:1815-1822.*

Rouet et al. Field Evaluation of a Rapid Human Immunodeficiency Virus (HIV) Serial Serologic Testing Algorithm for Diagnosis and Differentiation of HIV Type 1 (HIV-1), HIV-2, and Dual HIV-1-HIV-2 Infections in West African Pregnant Women. J. Clin. Microbiol. 2004; 42(9): 4147-4153).*

Sweep et al. Analytical Aspects of Biomarker Immunoassays in Cancer Research. In "Cancer Drug Discovery and Development: Biomarkers in Breast Cancer: Molecular Diagnostics for Predicting and Monitoring Therapeutic Effect" Edited by: G. Gasparini and D. F. Hayes © Humana Press Inc., Totowa, NJ. 2006; 17-30.*

Armstead et al. TPA Contributes to Impaired NMDA Cerebrovasodilation in Newborn Pig After Traumatic Brain Injury Through Activation of JNK MAPK. J. Neurotrauma, 2009; 26:A-74.*

WHO, HIV Assays: Operational Characteristics (Phase 1) Report 14 Simple/Rapid Tests; 2004.*

Zhang et al. Development of a colloidal gold-based lateral-flow immunoassay for the rapid simultaneous detection of clenbuterol and ractopamine in swine urine. Anal. Bioanal. Chem. 2009; 395:2591-2599.*

Hamelinck et al. Optimized Normalization for Antibody Microarrays and Application to Serum-Protein Profiling. Mol. Cell. Proteomics, 2005; 4: 773-784.*

Written Opinion in International Application No. PCT/EP2013/061175, Aug. 19, 2013, pp. 1-4.

* cited by examiner

METHOD FOR DIAGNOSING AND DIFFERENTIATING HIV-2 INFECTIONS

CROSS-REFERENCE TO RELATED APPLICATION

This application is the U.S. national stage application of International Patent Application No. PCT/EP2013/061175, filed May 30, 2013.

FIELD OF THE INVENTION

The present invention relates to the field of immunoassays and, in particular, to methods for diagnosing and differentiating HIV infections, in particular HIV-2 infections.

BACKGROUND OF THE INVENTION

Human Immunodeficiency Virus type 1 (HIV-1) is responsible for the majority of cases of HIV infection and AIDS throughout the world. It was thought to be the sole causative agent until 1986, when a second type of HIV was isolated, namely HIV type 2 (HIV-2).

HIV-2 is largely confined to West Africa but sporadic reports of HIV-2 infections have been made in several countries outside this area such as, for example, in Portugal, France, Mozambique, Angola, India and Brazil. However, due to antibody cross-reactivity to the proteins of HIV-1 and HIV-2, patients with HIV-2 infection may receive a diagnosis of HIV-1 infection and it is likely that the number of HIV-2 infections around the world is largely undercounted.

HIV-1 and HIV-2 are 50% similar at the genetic level with about 60% homology in conserved genes such as gag and pol, and about 39 to 45% homology in the envelope genes (Guyader et al., 1987). They share many features such as the route of transmission or the infected cell types but also maintain some distinct characteristics.

Although HIV-2 is less transmissible than HIV-1 and causes infections that progress more slowly, it can also lead to immunosuppression and clinical AIDS. Correct identification of HIV-2 infection is important because clinical management and treatment regimens differ for HIV-1 and HIV-2 infections. Indeed, some antiretroviral drugs, such as non-nucleoside reverse transcriptase inhibitors and some protease inhibitors, have a reduced efficacy in the treatment of HIV-2 infection (Ntemgwa et al, 2009).

The standard procedure for laboratory diagnosis of HIV infection usually consists of performing an HIV antibody immunoassay (a third or fourth-generation enzyme immunosorbent assay (EIA) or a rapid simple test) which, if reactive, is followed by confirmatory tests (Western blot or immunofluorescence assay). Western-blot (WB) or immunoblot is the most widely used confirmatory test. However, these tests are expensive, time-consuming and can yield indeterminate results due to HIV-2 antibody cross-reactivity to the proteins of HIV-1.

Based on the availability of new HIV tests, a new algorithm was proposed in 2010 in the USA to replace this standard procedure (Pandori and Branson, 2010). This algorithm includes a highly sensitive HIV-1/2 immunoassay such as a third or fourth-generation EIA, which, if reactive, is followed by a highly specific HIV-1/HIV-2 differentiation immunoassay. Specimens that are reactive for antibodies on both tests would be considered positive for either HIV-1 or HIV-2 antibodies. Specimens negative for antibody on the second test would then be tested with a nucleic acid amplification test (Delaney et al., 2011). This new algorithm was tested and was shown to outperform the previous algorithm because it was more sensitive for detecting HIV-1 infection, provided a great number of definitive results and detected HIV-2 more efficiently (Styer et al., 2011).

To date, several assays are available to differentiate HIV-1 from HIV-2 infections such as for example the Multispot® HIV-1/HIV-2 Rapid Test (Bio-Rad Laboratories), the Recombigen® HIV-1/HIV-2 RTD test (Cambridge Biotech), the PEPTI-LAV® 1-2 test (Bio-Rad Laboratories), the INNO-LIA® HIV Confirmation test (Innogenetics) or the Immunocomb® II HIV-1 & 2 BiSpot test (Orgenics). The INNO-LIA HIV I/II Score assay has been approved for diagnostic use in the European Union but currently cannot be used in the US. To date, only one assay that is capable of differentiating HIV-1 from HIV-2 infections has been approved by the FDA, namely the Multispot® HIV-1/HIV-2 Rapid Test (Bio-Rad Laboratories). This flow-through test differentiates HIV-1 from HIV-2 antibodies by using a synthetic peptide representing the immunodominant epitope of the HIV-2 virus gp36 envelope glycoprotein, a recombinant gp41 (HIV-1) envelope glycoprotein and a synthetic peptide representing the immunodominant epitope of the HIV-1 virus gp41 envelope glycoprotein. However, with these assays, a significant proportion of specimens remain undifferentiated. Furthermore, the Multispot® assay often requires an error-prone and time-consuming dilution.

Therefore, there remains a need for a simple, quick and cost-effective diagnostic test providing highly sensitive and specific results to differentiate HIV-1/HIV-2 cross reactivity from HIV-2 true reactivity and thus reducing the percentage of indeterminate specimens. This test should be suitable for use in multi-test algorithms designed for statistical validation of rapid HIV test results.

SUMMARY OF THE INVENTION

The inventors have herein demonstrated that the reactivity of antibodies present in a sample and capable of binding to HIV-1 envelope antigen immobilized on the solid support of an immunoassay device can be used to differentiate HIV-1/HIV-2 cross-reactivities from HIV-2 true reactivities. The present invention thus provides a new method for interpreting immunoassay results and reducing the percentage of undifferentiated specimens.

Accordingly, in a first aspect, the present invention concerns a method for differentiating infection with HIV-2 from infection with both HIV-1 and HIV-2 in a subject suspected of being either HIV-2 positive or HIV-1/HIV-2 positive, comprising
  (a) contacting a fluid sample from the subject with at least one HIV-1 envelope antigen and a control reagent that can bind human immunoglobulins, wherein said antigen and said control reagent are immobilized on distinct sites on a solid support, for a time and under conditions allowing the formation of complexes between antibodies present in the sample and (i) said HIV-1 antigen and (ii) said control reagent;
  (b) detecting the formation of said complexes using a system generating quantifiable signal;
  (c) normalizing the intensity of the signal obtained for said at least one HIV-1 envelope antigen by dividing by the intensity of the signal obtained for the control reagent thereby obtaining normalized value for said at least one HIV-1 envelope antigen;
  (d) if several HIV-1 envelope antigens are used, optionally calculating the mean value of normalized values for HIV-1 envelope antigens;

wherein a normalized or mean value for HIV-1 envelope antigen(s) lower than a predetermined threshold is indicative that the subject is infected with HIV-2 alone.

The sample may be further contacted with at least one HIV-2 antigen, preferably at least one HIV-2 envelope antigen.

Preferably, the fluid sample is selected from the group consisting of whole blood, serum and plasma.

The solid support may comprise at least one HIV-1 envelope antigen selected from the group consisting of recombinant gp160, gp120 and gp41, an antigenic fragment thereof, and a peptide comprising an immunodominant epitope of gp160, gp120 or gp41. It may also comprise at least one HIV-2 antigen selected from the group consisting of recombinant gp36, gp105 and gp140, an antigenic fragment thereof, and a peptide comprising an immunodominant epitope of gp36, gp105 or gp140.

In particular, in step a), the fluid sample may be contacted with recombinant gp160, an antigenic fragment thereof, or a peptide comprising an immunodominant epitope of gp160, preferably recombinant gp160. In this case, according to a particular embodiment of the invention, the predetermined threshold for the normalized value for gp160 antigen is about 0.3, preferably is between 0.24 and 0.36, more preferably is between 0.27 and 0.33 and even more preferably is between 0.28 and 0.32. Optionally, the fluid sample may be further contacted with recombinant gp41, an antigenic fragment thereof, or a peptide comprising an immunodominant epitope of gp41, preferably a peptide comprising an immunodominant epitope of gp41. In this case, according to a particular embodiment of the invention, the predetermined threshold for the mean value for gp160 and gp41 antigens is about 0.6, preferably is between 0.48 and 0.72, more preferably is between 0.54 and 0.66 and even more preferably is between 0.57 and 0.63 or between 0.58 and 0.62.

In the present method, the fluid sample may also be further contacted with at least one HIV-1 core antigen and/or at least one HIV-1 pol antigen immobilized on the support. In particular, the fluid sample may be further contacted with at least one HIV-1 antigen selected from the group consisting of recombinant p31 and p24, an antigenic fragment thereof and a peptide comprising an immunodominant epitope of p31 or p24.

Preferably, the immunoassay is a migration type assay, a flow-through test, a dipstick assay or a microfluidic assay, more preferably a migration type assay. In particular, the migration type assay may be a dual-path immunoassay.

The control reagent may be selected from the group consisting of protein A, protein G, protein A/G, protein L and derivatives thereof, and an anti-human immunoglobulin antibody. Preferably, the control reagent is protein A.

In step (b), the system generating quantifiable signal may be a reagent capable of binding to human immunoglobulins conjugated with a detectable label. In particular, the reagent may be selected from the group consisting of protein A, protein G, protein A/G, protein L and derivatives thereof, and an anti-human immunoglobulin antibody. Preferably, the reagent capable of binding to human immunoglobulins is protein A. The detectable label may be selected from the group consisting of colloidal metals; non-metallic colloids; carbon; visible, fluorescent, luminescent and chemiluminescent dyes; magnetic particles; radioactive elements; and enzymes. In a particular embodiment, the system generating quantifiable signal is a conjugate comprising a protein selected from the group consisting of protein A, protein G, protein A/G, protein L and derivatives thereof, coupled with a colloidal metal or a fluorescent, luminescent or chemiluminescent dye. In a more particular embodiment, the system generating quantifiable signal is protein A conjugated with colloidal gold.

BRIEF DESCRIPTION OF THE DRAWINGS

FIG. 1: Representation of a dual path HIV-1/2 immunoassay device.

DETAILED DESCRIPTION OF THE INVENTION

Due to the HIV-2 antibody cross-reactivity with HIV-1 antigens, differentiating HIV-2 infections and HIV-1/HIV-2 co-infections using an immunoassay remains a challenge and often leads to a significant percentage of indeterminate specimens.

The inventors analyzed a panel comprising a total of 475 HIV positive samples (185 HIV-1, 286 HIV-2 and 4 HIV- 1/HIV-2) using a migration type assay, in particular a dual-path immunoassay, designed to detect and discriminate HIV-1 and HIV-2 antibodies present in said samples. On 286 HIV-2 positive samples, 193 (67.5%) were reactive with both HIV-1 and HIV-2 antigens and thus remained undifferentiated.

In order to reduce the percentage of indeterminate specimens, the inventors calculated the ratio of the signal intensity obtained for antibodies directed against HIV-1 envelope antigens, in particular gp160 and/or gp41, to the signal intensity of the positive control. Hence, they calculated, for each sample, the ratio of the signal intensity obtained for complexes between antibodies present in the sample and HIV-1 envelope antigens (in particular gp160 and/or gp41) to the signal intensity obtained for complexes between antibodies present in the sample and the control reagent that binds human immunoglobulins. They found that this ratio could be used to differentiate HIV-1/HIV-2 cross-reactivities from HIV-2 true reactivities. They determined threshold value for this ratio and samples with ratio lower than this threshold are considered as HIV-2 positive. Using this method to interpret test results, only 16 samples (5.6%) on a total of 286 HIV-2 positive samples remained undifferentiated.

DEFINITIONS

As used herein, the term "subject" or "patient" refers to a human, including adult, child and human at the prenatal stage. Preferably, the HIV serological status (i.e., "HIV negative" or "HIV positive") of the subject has been previously determined as described hereafter. The method of the invention is particularly suitable for subjects suspected of being either HIV-2 positive or HIV-1/HIV-2 positive.

The term "HIV-positive subject", as used herein, refers to a subject being infected with Human Immunodeficiency Virus of any type. This infection may be diagnosed using any method known by the skilled person such as enzyme immunoassay, Western-blot or nucleic acid test. The term "HIV-2 positive" as used herein refers to a subject being infected only with HIV-2, or a sample from said subject. The term "HIV-1 positive" as used herein refers to a subject being infected only with HIV-1, or a sample from said subject. The term "HIV-1/HIV-2 positive" as used herein refers to a subject being infected with both HIV-1 and HIV-2, or a sample from said subject.

The term "fluid sample", "sample" or "specimen", as used herein, refers to any fluid sample comprising antibodies derived from the subject such as whole blood, serum, plasma, saliva, milk, amniotic fluid, urine or seminal fluid samples. This term may also refer to a culture fluid in which any cells or tissue preparation from the subject has been incubated. Preferably, the fluid sample is a sample of whole blood, serum or plasma. The sample may be fresh or frozen sample. It can be used immediately after collection or can be stored before to be tested. In particular, fresh samples may be stored up to 48 hours at room temperature (20-30° C.) or up to 7 days at 2-8° C. For long-term storage, samples may be frozen (−20° C. or lower) and thawed before use. The sample may be treated prior to use such as preparing plasma or serum from blood, diluting viscous fluid, or the like. Preferably, the sample is not treated prior to use and in particular is not heat inactivated.

The term "HIV-1/HIV-2 cross-reactive antibodies" as used herein, refers to antibodies that react with at least one HIV-1 antigen and at least one HIV-2 antigen.

As used herein, the term "HIV antigen" refers to a peptide or protein comprising an epitope that is recognized by an anti-HIV antibody. In particular, the term "HIV-1 antigen" refers to peptide or protein comprising an epitope that is recognized by an antibody directed against a glycoprotein of HIV-1 and the term "HIV-2 antigen" refers to peptide or protein comprising an epitope that is recognized by an antibody directed against a protein or glycoprotein of HIV-2. The term "HIV-1 envelope antigen" refers to peptide or protein comprising an epitope that is recognized by an antibody directed against a glycoprotein of the HIV-1 envelope and the term "HIV-2 envelope antigen" refers to peptide or protein comprising an epitope that is recognized by an antibody directed against a protein or glycoprotein of the HIV-2 envelope. The antigen may be produced by chemical process, by genetic recombination, or may be purified from a biological sample.

In a particular embodiment, the HIV antigen is selected from the group consisting of a recombinant, synthetic or purified protein of HIV virus, or any antigenic fragment thereof. The term "antigenic fragment" is intended to mean a fragment of a protein or glycoprotein which is able to be recognized by antibodies directed against said protein or glycoprotein, and to allow affinity binding with the latter. Preferably, the antigenic fragment has a size of at least 7 amino acid residues. More preferably, the antigenic fragment has a size in the range of 7 to 40 amino acid residues. Even more preferably, said antigenic fragment comprises an immunodominant epitope.

A "recombinant protein" means a polypeptide produced by expression in a recombinant expression system such as, for example, human cell lines transfected with an expression vector encoding the polypeptide of interest. HIV recombinant proteins may be expressed in various host cells such as, for example, bacteria (e.g. *E. coli*), human cells, yeast or insect cells (using a baculovirus expression system (Arora and Seth, 2003)).

A "synthetic protein" means a polymeric form of amino acids of any length which may be chemically synthesized using well known methods.

A "purified protein" means a naturally occurring polypeptide purified from supernatants of HIV-infected cells or a recombinant protein purified from the supernatants of cells transfected with an expression vector encoding the polypeptide of interest. This polypeptide is essentially free of cellular component with which it is naturally associated. In particular, the purified polypeptide is free of any component which could non-specifically interact with HIV antibodies and lead to false positive or negative results. Methods of protein purification are well known in the art.

The term "control reagent", as used herein, refers to a reagent that can bind human immunoglobulins from the sample, in particular HIV and non HIV antibodies, in order to determine the validity of the assay. Preferably, the control reagent can bind the Fc region of human immunoglobulins, in particular human IgG. Examples of compound that may be used as control reagent include, but are not limited to, protein A, protein G, protein A/G, protein L, and their derivatives; or an anti-human immunoglobulin antibody, preferably an antibody directed against the Fc region of human immunoglobulins. In a particular embodiment, the control reagent is protein A.

The term "conjugate", as used herein, refers to a compound designed to bind to an analyte of interest, in particular a human immunoglobulin, and to produce a detectable signal. The conjugate typically comprises a specific binding member conjugated to a label.

The term "immunodominant epitope" refers to a highly conserved and/or highly immunogenic region of a protein or glycoprotein. Due to extensive studies, numerous immunodominant epitopes of HIV proteins and glycoproteins are well-known (see for example Robinson et al., 1990; Xu et al., 1991; Barin et al., 1996; Tomaras et al., 2008; Penn-Nicholson et al., 2008; Benjouad et al., 1993; Espejo and Uribe, 1990). The skilled person may thus easily design peptides comprising an immunodominant epitope suitable for use in the present invention. The peptides used in the present invention may comprise one or several immunodominant epitopes.

As used in this specification, the term "about" refers to a range of values ±20% of the specified value. For example, "about 20" includes ±20% of 20, or from 16 to 24. More preferably, the term "about" refers to a range of values ±10% of the specified value, even more preferably, a range of values ±5% or ±3% of the specified value.

By "at least one", it is meant herein one or several.

By "several", it is meant herein two, three or more than three, preferably two.

The methods of the invention as disclosed below are preferably in vitro methods.

In a first aspect, the present invention concerns a method for differentiating infection with HIV-2 from infection with both HIV-1 and HIV-2 in a subject suspected of being either HIV-2 positive or HIV-1/HIV-2 positive, comprising (a) contacting a fluid sample from the subject with at least one HIV-1 envelope antigen and a control reagent that can bind human immunoglobulins, wherein said antigen and said control reagent are immobilized on distinct sites on a solid support, for a time and under conditions allowing the formation of complexes between antibodies present in the sample and (i) said HIV-1 antigen and (ii) said control reagent;

(b) detecting the formation of said complexes using a system generating quantifiable signal;

(c) normalizing the intensity of the signal obtained for said at least one HIV-1 envelope antigen by dividing by the intensity of the signal obtained for the control reagent thereby obtaining normalized value for said at least one HIV-1 envelope antigen;

(d) if several HIV-1 envelope antigens are used, optionally calculating the mean value of normalized values for HIV-1 envelope antigens;

wherein a normalized or mean value for HIV-1 envelope antigen(s) lower than a predetermined threshold is indicative that the subject is infected with HIV-2 alone.

A normalized or mean value for HIV-1 envelope antigen(s) higher than a predetermined threshold is indicative that the subject is infected with both HIV-1 and HIV-2 or that, for this subject, at least one additional test is needed to discriminate HIV-1/HIV-2 cross-reactivity from HIV-2 true reactivity.

The immunoassay device used in the method of the invention is a solid-phase immunoassay device incorporating a solid support to which HIV antigens and control reagent are bound. The solid support may be of any form such as plate, tube or bead, and numerous suitable materials may be used such as nitrocellulose, nylon, cellulose acetate, glass fibers, or other porous polymers.

In particular, the immunoassay may be a migration type assay, a flow-through test, a dipstick assay or a microfluidic assay. Preferably, the immunoassay is a migration type assay or a flow-through test, more preferably, a migration type assay.

A migration type assay device typically comprises a sample pad, a conjugate pad, a membrane to which HIV antigens and control reagent are bound on distinct sites (usually distinct lines), an absorbent pad and, optionally, a buffer pad if different from the sample pad. The migration type assay device may be, for example, a lateral flow strip or a dual-path immunoassay device as described in the international patent application WO 2006/099191. In a preferred embodiment, the immunoassay is a dual-path immunoassay.

A flow-through immunoassay device usually comprises a membrane or filter to which HIV antigens and control reagent are bound on distinct sites (usually distinct spots), and an absorbent pad. The fluid sample is applied to the membrane and allowed to wick through by capillary action. A conjugate is then applied to reveal the presence of HIV antibodies. Optional wash step(s) can be performed before and/or after adding the conjugate.

A dipstick assay device typically comprises a solid, non porous support onto which HIV antigens and control reagent are bound on distinct sites (usually distinct spots). To perform the assay, the device is successively dipped into the fluid sample, a wash solution, a solution containing the conjugate, and optionally a second wash solution.

A microfluidic assay involves a "lab on a chip" device, a network of micron-dimension channels. HIV antigen(s) and control reagent(s) may be immobilized on the surface of said microchannels (see for example Ng et al., 2010; Song et al., 2012).

All these types of immunoassays are well known by the skilled person.

In step a) of the method of the invention the fluid sample from the subject is contacted with at least one HIV-1 envelope antigen immobilized on the solid support of the immunoassay device. This HIV-1 envelope antigen may be an envelope glycoprotein of HIV-1, or an antigenic fragment thereof, or may also be a peptide comprising an epitope recognized by an antibody directed against said HIV-1 envelope glycoprotein, in particular a peptide comprising an immunodominant epitope of said glycoprotein.

The HIV-1 envelope glycoprotein may be any protein encoded by the env gene of HIV-1, i.e. the envelope glycoprotein precursor gp160, the external envelope protein gp120 or the transmembrane envelope protein gp41. The glycoprotein may be produced by recombinant techniques, chemically synthesized, or purified from biological samples. Preferably, the glycoprotein is a recombinant protein.

In an embodiment, the sample is contacted with at least one HIV-1 envelope antigen selected from the group consisting of recombinant gp160, gp120 and gp41, an antigenic fragment thereof, and a peptide comprising an immunodominant epitope of gp160, gp120 or gp41. Preferably, the sample is contacted with at least one HIV-1 envelope antigen selected from the group consisting of recombinant gp160 and gp41, an antigenic fragment thereof, and a peptide comprising an immunodominant epitope of gp160 or gp41.

In a particular embodiment, the sample is contacted with at least one HIV-1 envelope antigen selected from the group consisting of recombinant gp160, an antigenic fragment thereof, and a peptide comprising an immunodominant epitope of gp160. Preferably, the sample is contacted with recombinant gp160. Optionally, the sample may be further contacted with another one HIV-1 envelope antigen, preferably an antigen selected from the group consisting of recombinant gp41, an antigenic fragment thereof, and a peptide comprising an immunodominant epitope of gp41, more preferably a peptide comprising an immunodominant epitope of gp41. In a more particular embodiment, the sample is contacted with recombinant gp160 and a peptide comprising an immunodominant epitope of gp41.

In another particular embodiment, the sample is contacted with at least one HIV-1 envelope antigen selected from the group consisting of recombinant gp41, an antigenic fragment thereof, and a peptide comprising an immunodominant epitope of gp41.

Optionally, the sample may be further contacted with at least one another HIV-1 antigen immobilized on the support of the immunoassay device. The additional HIV-1 antigen(s) may be selected from the group consisting of recombinant, synthetic or purified proteins encoded by the gag or pol gene of HIV-1 (e.g. p66, p55, p51, p40, p31/34 ("p31"), p24/25 ("p24") or p18), any antigenic fragment thereof, and any peptide comprising an immunodominant epitope of said proteins. In a particular embodiment, the sample is further contacted with at least one HIV-1 antigen selected from the group consisting of recombinant p31 and p24, an antigenic fragment thereof, and a peptide comprising an immunodominant epitope of p31 or p24. Preferably, the sample is further contacted with a peptide comprising an immunodominant epitope of p31 and recombinant p24.

The sample may be also contacted with at least one HIV-2 antigen. HIV-2 antigen may be a recombinant, synthetic or purified protein (or glycoprotein) of HIV-2, or an antigenic fragment thereof. The HIV-2 antigen may also be a peptide comprising an epitope recognized by an antibody directed against a protein of HIV-2, in particular a peptide comprising an immunodominant epitope of said protein.

In particular, the HIV-2 protein may be selected from the group consisting of the gag proteins (p56, p26 and p16), the pol proteins (p68 and p34) and the envelope glycoproteins (gp140, gp105/125 ("gp105") and gp36). Preferably, HIV-2 antigen is chosen in order to limit cross-reactions with HIV-1 antibodies.

In an embodiment, in step a), the sample is further contacted with at least one HIV-2 antigen selected from the group consisting of recombinant proteins encoded by the env gene of HIV-2, i.e. the envelope glycoprotein precursor gp140, the external envelope protein gp105 and the transmembrane envelope protein gp36, an antigenic fragment thereof, and a peptide comprising an immunodominant epitope of gp140, gp105 or gp36. Preferably, the sample is further contacted with at least one HIV-2 antigen selected from the group consisting of recombinant gp36 and gp140, an antigenic fragment thereof, and a peptide comprising an immunodominant epitope of gp36 or gp140.

In a particular embodiment, the sample is further contacted with at least one HIV-2 antigen selected from the group consisting of recombinant gp36, an antigenic fragment thereof, and a peptide comprising an immunodominant epitope of gp36, preferably a peptide comprising an immunodominant epitope of gp36. Optionally, the sample may be further contacted with another HIV-2 envelope antigen, preferably an antigen selected from the group consisting of recombinant gp140, an antigenic fragment thereof, and a peptide comprising an immunodominant epitope of gp140, more preferably a peptide comprising an immunodominant epitope of gp140.

The amounts of HIV-antigen(s) and control reagent immobilized on the solid support are easily chosen by the skilled person in order to provide the best immunoreactivity.

Time and conditions allowing the formation of complexes between antibodies from the sample and immobilized antigens/reagents, depend on the immunoassay device used in the method of the invention and are easily adjusted by the skilled person.

The formation of complexes between antibodies from the sample and (i) HIV-antigen(s) and (ii) the control reagent is then detected using a system generating quantifiable signal. This system is chosen in order to produce a detectable signal at a level, or intensity, relative to the amount of antibody linked to each immobilized reagent/antigen. Preferably, the same system is used to generate signals for HIV antigen-antibody complexes and control reagent-antibody complexes.

Typically, the system generating quantifiable signal comprises a specific binding member conjugated to a signal generating compound. In particular, this system may be a reagent capable of binding to human immunoglobulins, preferably to the Fc region of human immunoglobulins, conjugated with a detectable label.

In an embodiment, the reagent capable of binding to human immunoglobulins is a protein selected from the group consisting of proteins which are able to bind the Fc region of human immunoglobulins such as protein A, protein G, protein A/G, protein L, and their derivatives, or antibodies directed against human immunoglobulins, in particular antibodies directed against the Fc region of human immunoglobulins.

If the specific binding member is an antibody, it can be a monoclonal antibody, polyclonal antibody, an antibody fragment, a recombinant antibody, or a mixture thereof. The details of the preparation of such antibodies and their suitability for use as specific binding members are well known to those in the art.

In a preferred embodiment, the reagent capable of binding to human immunoglobulins is selected from the group consisting of protein A, protein G, protein A/G, protein L, and their derivatives, preferably is protein A.

The detectable label conjugated with the reagent capable of binding to human immunoglobulins may be any compound generating a signal quantifiable, preferably by instrumented reading. Suitable detectable labels may be selected, for example, from the group consisting of colloidal metals such as gold or silver; non-metallic colloids such as colloidal selenium, tellurium or sulphur particles; carbon; visible, fluorescent, luminescent and chemiluminescent dyes; magnetic particles; radioactive elements; and enzymes.

In a particular embodiment, the system generating quantifiable signal is a conjugate comprising a protein which is able to bind the Fc region of human immunoglobulins, preferably selected from the group consisting of protein A, protein G, protein A/G, protein L and derivatives thereof, coupled with a colloidal metal or a fluorescent, luminescent or chemiluminescent dye. In a preferred embodiment, the system generating quantifiable signals is a conjugate comprising protein A coupled with colloidal gold.

The signal intensity for each complex between antibodies from the sample and immobilized reagent/antigen, may be measured using a suitable instrumented reader, in particular a reader that is capable of capturing and analyzing images. The choice of the instrumented reader depends on the nature of the signal emitted by the detectable label and the immunoassay device used in the present method.

The signal intensity obtained for HIV-1 envelope antigen-antibody complex is normalized by dividing by the signal intensity obtained with control reagent-antibody complex. If several HIV-1 envelope antigens are immobilized on the support, normalized value of the signal intensity may be calculated for each of these antigens.

In an embodiment, normalized value is calculated for gp160 and/or gp41 antigen. The term "gp160 antigen", as used herein, preferably refers to an antigen selected from the group consisting of recombinant gp160, an antigenic fragment thereof, and a peptide comprising an immunodominant epitope of gp160. The term "gp41 antigen", as used herein, preferably refers to an antigen selected from the group consisting of recombinant gp41, an antigenic fragment thereof, and a peptide comprising an immunodominant epitope of gp41.

When several HIV-1 envelope antigens are immobilized on the solid support and are to be considered, the mean value of normalized values is calculated, i.e. the sum of normalized values of n HIV-1 antigens divided by n.

The inventors observed that normalized or mean value of the signal intensity(ies) obtained for HIV-1 envelope antigen(s) can be used to differentiate HIV-1/HIV-2 cross-reactivities from HIV-2 true reactivities. They found that, in cases of HIV-2 cross-reactivity, this value is statistically significantly lower than that observed in HIV-1 and HIV-1/HIV-2 positive samples. Accordingly, a normalized or mean value for a sample lower than a predetermined threshold value is indicative of infection with HIV-2 alone. On the contrary, a normalized or mean value for a sample higher than a predetermined threshold value is indicative of infection with both HIV-1/HIV-2 or that, for said sample, additional test is needed to differentiate HIV-1/HIV-2 cross-reactivity from HIV-2 true reactivity.

The threshold value for segregating HIV-2 positive samples from other samples, is determined depending on the choice and the number of HIV-1 envelope antigens. Preferably, this threshold value is chosen in order to satisfy two requirements (i) a frequency of HIV-2 positive samples with a normalized or mean value above the threshold value as low as possible, and (ii) a frequency of HIV-1 and HIV-1/HIV-2 positive samples with a normalized or mean value below the threshold value as low as possible. In particular, this threshold value may be determined as the lowest crossing point of the curves representing the cumulated frequencies of (i) HIV-1 and/or HIV-1/HIV-2 positive samples and (ii) HIV-2 positive samples to the normalized or mean values.

In an embodiment, the immunoassay is a migration type assay, preferably a dual-path immunoassay as described in the international patent application WO 2006/099191, and (1) the normalized value is calculated for a gp160 antigen and the predetermined threshold value is about 0.3, preferably between 0.24 and 0.36, more preferably between 0.27 and 0.33 and even more preferably between 0.28 and 0.32 or between 0.29 and 0.31;

(2) the normalized value is calculated for a gp41 antigen and the predetermined threshold value is about 0.9, preferably between 0.72 and 1.08, more preferably between 0.81 and 0.99 and even more preferably between 0.85 and 0.95 or between 0.87 and 0.93; or (3) the mean value is calculated for gp160 and gp41 antigens and the predetermined threshold value is about 0.6, preferably between 0.48 and 0.72, more preferably between 0.54 and 0.66 and even more preferably between 0.57 and 0.63 or between 0.58 and 0.62.

In a particular embodiment, the method of the invention comprises (a) contacting a fluid sample from a subject with at least one gp160 antigen, preferably recombinant gp160, and a control reagent which is protein A, wherein said antigen and said control reagent are immobilized on distinct sites on a solid support, for a time and under conditions allowing the formation of complexes between antibodies present in the sample and (i) said HIV-1 antigen and (ii) said control reagent;

(b) detecting the formation of said complexes using a system generating quantifiable signal, wherein said system is protein A conjugated with colloidal gold;

(c) normalizing the intensity of the signal obtained for gp160 antigen by dividing by the intensity of the signal obtained for protein A thereby obtaining normalized value for gp160 antigen;

wherein a normalized value for gp160 antigen lower than a predetermined threshold of about 0.3 is indicative that the subject is infected with HIV-2 alone. Preferably, the predetermined threshold is between 0.24 and 0.36, more preferably between 0.27 and 0.33 and even more preferably between 0.28 and 0.32 or between 0.29 and 0.31.

In another particular embodiment, the method of the invention comprises (a) contacting a fluid sample from a subject with at least one gp41 antigen, preferably a peptide comprising an immunodominant epitope of gp41, and a control reagent which is protein A, wherein said antigen and said control reagent are immobilized on distinct sites on a solid support, for a time and under conditions allowing the formation of complexes between antibodies present in the sample and (i) said HIV-1 antigen and (ii) said control reagent;

(b) detecting the formation of said complexes using a system generating quantifiable signal, wherein said system is protein A conjugated with colloidal gold;

(c) normalizing the intensity of the signal obtained for gp41 antigen by dividing by the intensity of the signal obtained for protein A thereby obtaining normalized value for gp41 antigen;

wherein a normalized value for gp41 antigen lower than a predetermined threshold of about 0.9 is indicative that the subject is infected with HIV-2 alone. Preferably, the predetermined threshold is between 0.72 and 1.08, more preferably between 0.81 and 0.99 and even more preferably between 0.85 and 0.95 or between 0.87 and 0.93.

In a further particular embodiment, the method of the invention comprises (a) contacting a fluid sample from a subject with at least one gp160 antigen, preferably recombinant gp160, at least one gp41 antigen, preferably a peptide comprising an immunodominant epitope of gp41, and a control reagent which is protein A, wherein said antigens and said control reagent are immobilized on distinct sites on a solid support, for a time and under conditions allowing the formation of complexes between antibodies present in the sample and (i) said HIV-1 antigens and (ii) said control reagent;

(b) detecting the formation of said complexes using a system generating quantifiable signal, wherein said system is protein A conjugated with colloidal gold;

(c) normalizing the intensity of the signal obtained for gp160 antigen and the intensity of the signal obtained for gp41 antigen by dividing by the intensity of the signal obtained for protein A thereby obtaining normalized values for gp160 antigen and gp41 antigen;

(d) calculating the mean value of normalized values for gp160 and gp41 antigens;

wherein a mean value for gp160 and gp41 antigens lower than a predetermined threshold of about 0.6 is indicative that the subject is infected with HIV-2 alone. Preferably, the predetermined threshold is between 0.48 and 0.72, more preferably between 0.54 and 0.66 and even more preferably between 0.57 and 0.63 or between 0.58 and 0.62.

In another aspect, the present invention concerns a method for diagnosing HIV-2 infection in a subject suspected to develop HIV-1/HIV-2 cross-reactive antibodies, comprising (a) contacting a fluid sample from said subject with at least one HIV-1 envelope antigen and a control reagent that can bind human immunoglobulins, wherein said antigen and said control reagent are immobilized on distinct sites on a solid support, for a time and under conditions allowing the formation of complexes between antibodies present in the sample and (i) said HIV-1 antigen and (ii) said control reagent;

(b) detecting the formation of said complexes using a system generating quantifiable signal;

(c) normalizing the intensity of the signal obtained for said at least one HIV-1 envelope antigen by dividing by the intensity of the signal obtained for the control reagent thereby obtaining normalized value for said at least one HIV-1 envelope antigen;

(d) if several HIV-1 envelope antigens are used, optionally calculating the mean value of normalized values for HIV-1 envelope antigens;

wherein a normalized or mean value for HIV-1 envelope antigen(s) lower than a predetermined threshold is indicative that the subject is infected with HIV-2 alone.

All the embodiments of the method of the invention according to the first aspect are also contemplated in this aspect.

Further aspects and advantages of the present invention will be described in the following examples, which should be regarded as illustrative and not limiting.

EXAMPLES

Materials and Methods

HIV Positive Samples

HIV positive subjects were obtained from commercial panels (Promedex or Bocabiolistics) or from hospitals (La Pitié Salpétrière, Bichat, Paris, France). The classification (HIV-1, HIV2 or HIV-1/HIV-2 positive) of each specimen was confirmed using Western-blot assays (New Lay Blot 1, New Lay Blot 2, Bio-Rad Laboratories). Alternately, any other suitable Western-blot assays (including Genetic Systems HIV-1) and/or suitable PCR amplification assays may be used.

Two lots of "Geenius" immunoassay were evaluated: lot A and lot B. A first panel of samples comprises 293 HIV-positive samples (135 HIV-1, 154 HIV-2 and 4 HIV-1/HIV-2 dually reactive). A second panel of samples comprises 182 HIV-positive samples (50 HIV-1 and 132 HIV-2).

The "Geenius" Immunoassay Device

Experiments were carried out using a dual-path immunoassay device as described in the international patent application WO 2006/099191. This device is below referred as "Geenius" device.

Figure 1A:
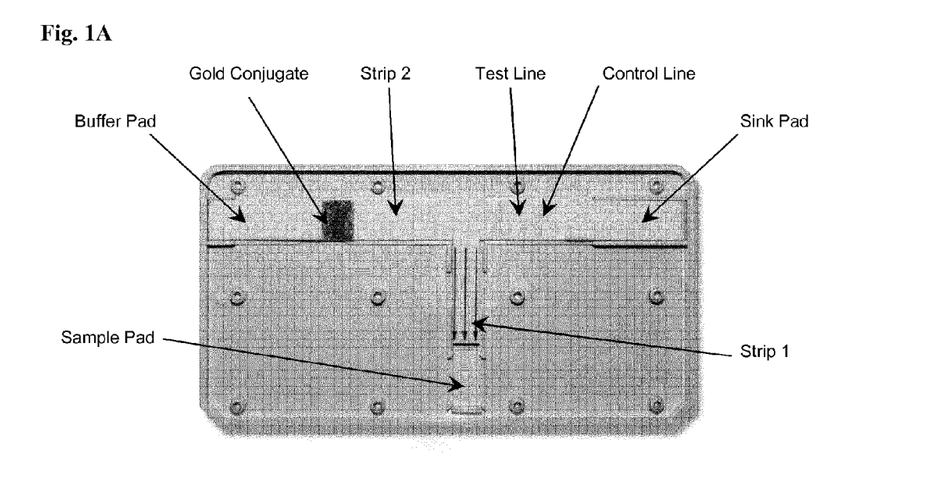
FIG. 1A: Picture of the HIV-1/2 Geenius™ device without upper house.

Briefly, this device comprises a first strip for the collection and transportation of the sample to be tested (FIG. 1A, Strip 1) and a second strip for the detection of antibodies against HIV-1 and HIV-2 (FIG. 1A, Strip 2). The first and second strips are laminated onto a plastic card and touch each other at the test site location.

Figure 1B:
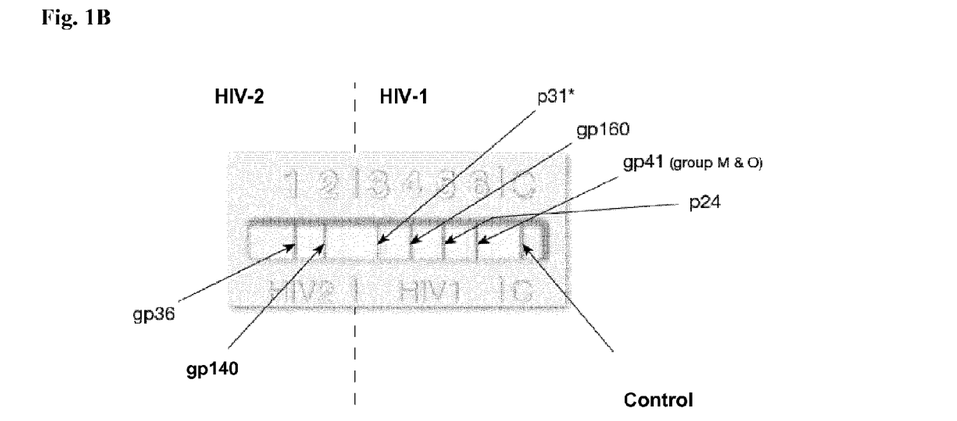
FIG. 1B: HIV-1 and HIV-2 test lines and control line of the HIV-1/2 Geenius™ device.

The first strip comprises of a sample pad of cellulose paper attached to a nitrocellulose membrane. The second strip comprises a buffer pad, a gold conjugate pad, test and control lines and a sink pad. The gold conjugate pad was obtained by spraying protein A conjugated with purple colloidal gold particles. Test lines were obtained by immobilizing HIV-1 and HIV-2 peptides or recombinant proteins. In particular, the device used in this example comprises: line 1: synthetic HIV-2 peptide gp36 (HIV-2 envelop); line 2: synthetic HIV-2 peptide gp140 (HIV-2 envelop); line 3: synthetic HIV-1 peptide p31 (HIV-1 polymerase); line 4: HIV-1 recombinant protein gp160 (HIV-1 envelop); line 5: HIV-1 recombinant protein p24 (HIV-1 core); and line 6: synthetic HIV-1 peptide gp41 (HIV-1 Group M&O envelop) (FIG. 1B). The control line consists of immobilized protein A.

Test Procedure with the Geenius Device

For each specimen, 5 µL of serum or plasma or 15 µL of whole blood were added on the sample pad of a Geenius device with 60 µL of buffer. After waiting between one and five minutes (preferably one or two minutes) until the sample reached the test zone (i.e., the test and control lines), 150 µL of the same buffer were added on the buffer pad thereby mobilizing the gold conjugate to the test and control lines. After about fifteen minutes, test results were read.

Basic interpretation of the results was based on the presence or the absence of purple color in test and control lines.

If only the control line showed purple color, the test was interpreted as HIV negative result. If at least 2 HIV-1 lines (one being envelop line) and the control line showed purple color, the test was interpreted as positive for HIV-1 antibodies. If the 2 HIV-2 lines and the control line showed purple color, the test was interpreted as positive for HIV-2 antibodies. If at least one HIV-1 line, at least one HIV-2 line and the control line showed purple color, the test was interpreted as undifferentiated HIV reactive result. These results were obtained using an automated reader that captured and analyzed images.

Test Procedures with Multispot® HIV-1/HIV-2 Rapid Test and INNO-LIA™ HIV I/II Score The assays were performed according to supplier's instructions.

Multispot assays were carried out on neat samples and 1:100 diluted samples.

Results

Classification of the HIV Samples Based on the Reactivity with HIV-1 and/or HIV-2 Test Lines of the Geenius Device The reactivity of all HIV-samples herein tested was confirmed by Western-blot or PCR amplification. All these samples were then tested using the "Geenius" device as described above. Using visual or automated reading, the appearance of purple color on HIV-1 and/or HIV-2 test lines was determined and samples were thus classified as HIV-1 reactive, HIV-2 reactive or undifferentiated HIV reactive.

In this study, none HIV-1 reactive sample showed cross-reactivity on HIV-2 lines whereas between 66.9 and 68.2% of HIV-2 reactive samples were classified as undifferentiated (Table 1).

Use of Color Intensities of Gp160 and Gp41 Bands to Improve HIV-1/2 Differentiation The color of each band results from the aggregation of protein A conjugated with purple colloidal gold particles. This aggregation is due to the binding of protein A to the Fc portion of immunoglobulins reacting with the immobilized antigen. The color intensity of each band thus depends on the quantity of antibodies present in the sample which is able to bind the immobilized antigen.

The intensity of the color was measured for gp160, gp41 and control bands for each HIV-1 positive or undifferentiated HIV-2 positive sample of lots A and B using an automated reader. Raw values obtained from gp160 and gp41 bands were normalized by calculating the ratio of the intensity values of gp160 and gp41 bands to the intensity value of the control band (gp160+gp41/control). The mean values for the two HIV-1 envelope antigens were then calculated ((gp160+gp41/control)/2).

Figure 2:
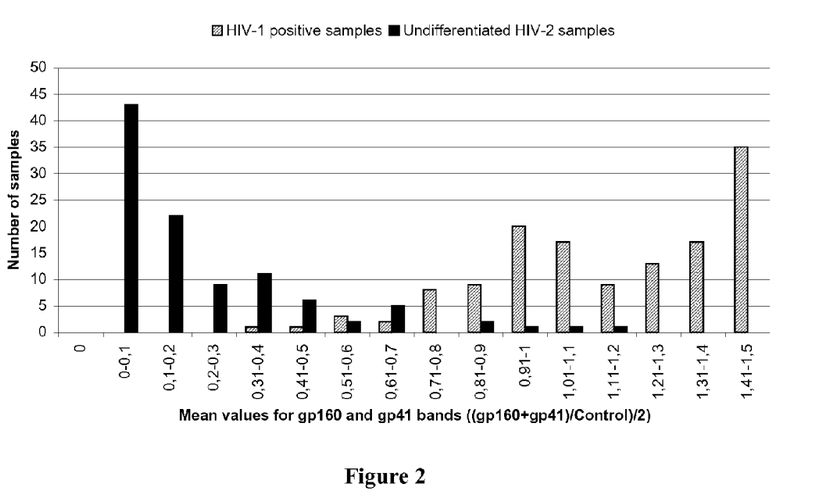
FIG. 2: Distribution of the mean values for normalized gp160 and gp41 band intensities ((intensity of the gp160 band+intensity of the gp41 band)/intensity of the control band)/2) in HIV-1 positive (n=135) and undifferentiated HIV-2 samples (103 undifferentiated samples on a total of 154 HIV-2 positive samples) of lot A.
Figure 3:
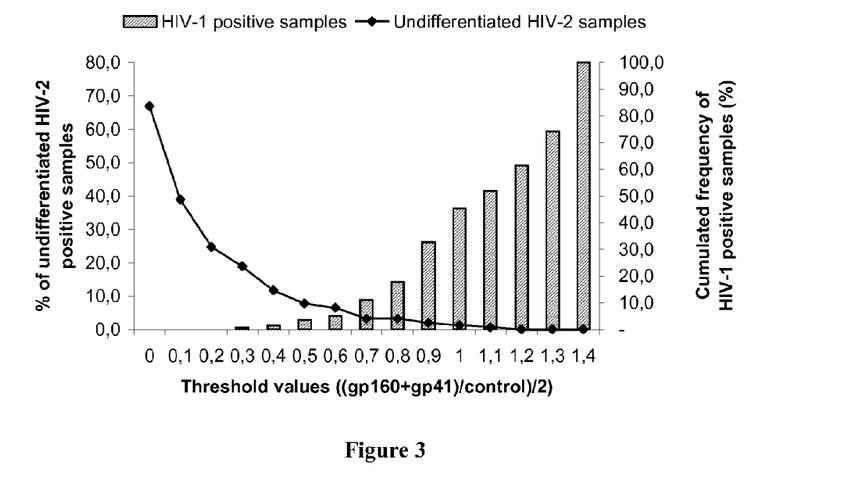
FIG. 3: Cumulated frequencies of HIV-1 positive samples (n=135) and percentage of undifferentiated HIV-2 positive samples (103 undifferentiated samples on a total of 154 HIV-2 positive samples) of lot A according to threshold values for the mean values for gp160 and gp41 band intensities ((intensity of the gp160 band+intensity of the gp41 band)/intensity of the control band)/2).
Figure 4:
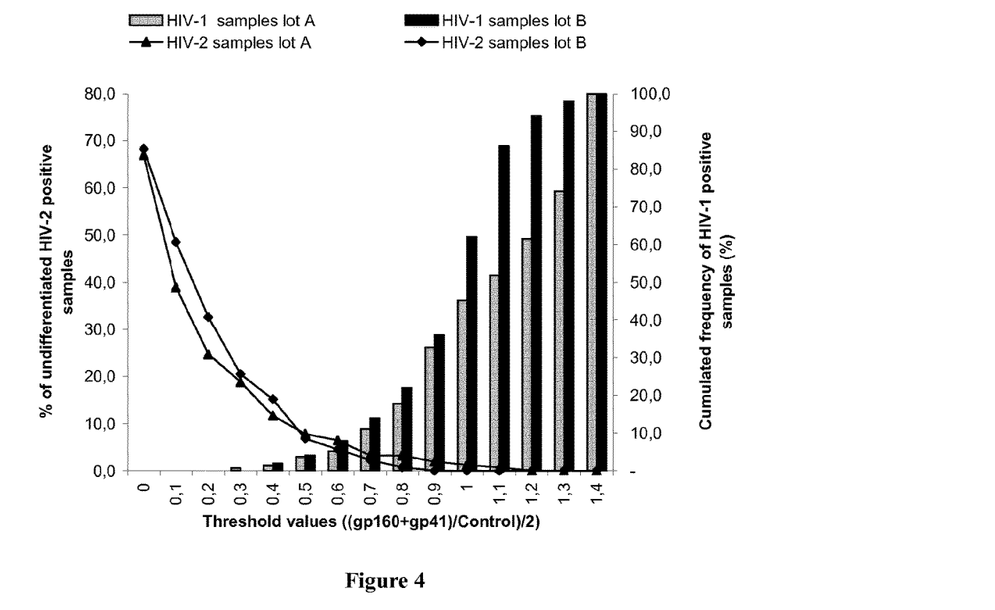
FIG. 4: Cumulated frequencies of HIV-1 positive samples of lot A (n=135) and lot B (n=50) and percentage of undifferentiated HIV-2 positive samples of lot A (103 undifferentiated samples on a total of 154 HIV-2 positive samples) and lot B (90 undifferentiated samples on a total of 132 HIV-2 positive samples) according to threshold values for the mean values for gp160 and gp41 band intensities ((intensity of the gp160 band+intensity of the gp41 band)/intensity of the control band)/2).

The mean values of undifferentiated HIV-2 samples were found to be significantly lower than the mean values of HIV-1 positive samples, demonstrating that this ratio could be used to differentiate cross-reactivities from true reactivities (FIGS. 2 to 4).

At a threshold value for the mean values ((gp160+gp41)/control)/2) of 0.6, only 6.5 and 4.5% of HIV-2 positive samples of lots A and B, respectively, remained undifferentiated (FIG. 4). Considering this threshold value, a sample having a mean value lower than 0.6 was interpreted as positive for HIV-2 antibodies.

Use of the Color Intensity of Gp160 Band to Improve HIV-1/2 Differentiation

The intensity of the color was measured for gp160 and control bands for each HIV-1 positive or undifferentiated HIV-2 positive sample of lots A and B using an automated reader. Raw values obtained from gp160 bands were normalized by calculating the ratio of the intensity value of gp160 band to the intensity value of the control band (gp160/control).

Figure 5:
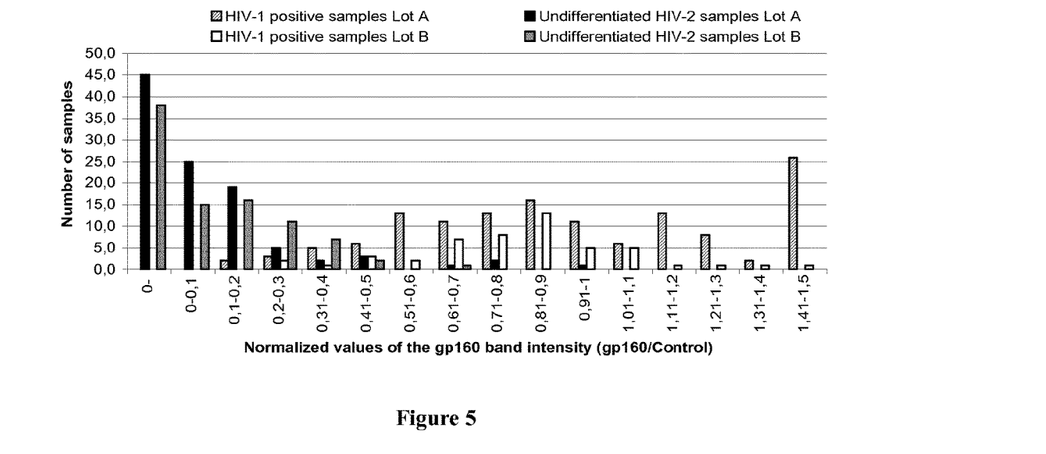
FIG. 5: Distribution of the normalized values of the gp160 band intensity (intensity of the gp160 band/intensity of the control band) in HIV-1 positive samples of lot A (n=135) and lot B (n=50) and undifferentiated HIV-2 samples of lot A (103 undifferentiated samples on a total of 154 HIV-2 positive samples) and B (90 undifferentiated samples on a total of 132 HIV-2 positive samples).

The normalized values of the gp160 band intensity of undifferentiated HIV-2 samples were found to be significantly lower than the normalized values of HIV-1 positive samples, demonstrating that this ratio could be used to differentiate cross-reactivities from true reactivities (FIG. 5).

Figure 6:
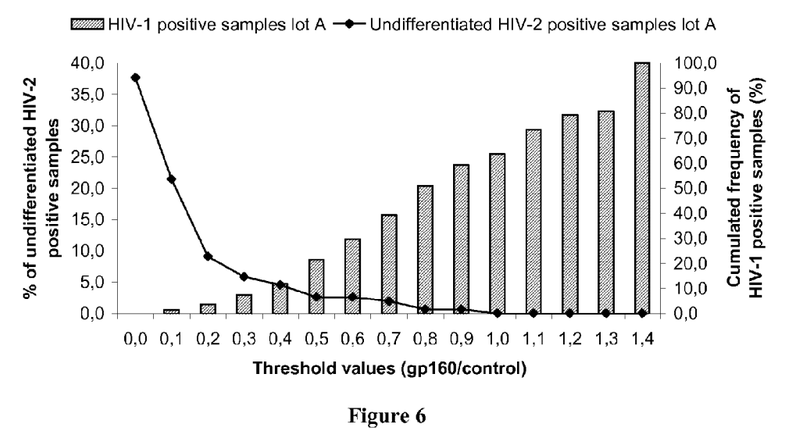
FIG. 6: Cumulated frequencies of HIV-1 positive samples (n=135) and percentage of undifferentiated HIV-2 positive samples of lot A (103 undifferentiated samples on a total of 154 HIV-2 positive samples) according to threshold values for the normalized values for gp160 band intensity (intensity of the gp160 band/intensity of the control band).
Figure 7:
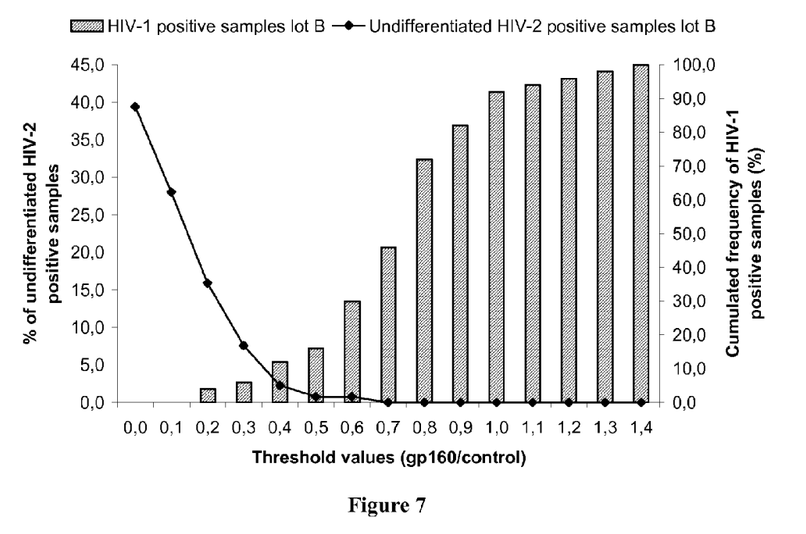
FIG. 7: Cumulated frequencies of HIV-1 positive samples (n=50) and percentage of undifferentiated HIV-2 positive samples of lot B (90 undifferentiated samples on a total of 132 HIV-2 positive samples) according to threshold values for the normalized values for gp160 band intensity (intensity of the gp160 band/intensity of the control band).

At a threshold value for the normalized values (gp160/control) of 0.3, only 5.8 and 7.6% of HIV-2 positive samples of lots A and B, respectively, remained undifferentiated (FIGS. 6 and 7). Considering this threshold value, a sample having a normalized value lower than 0.3 was interpreted as positive for HIV-2 antibodies.

HIV-1/HIV-2 Co-Infection

Due to the low proportion of HIV-1/HIV-2 co-infection, the panels comprised only 4 HIV-1/HIV-2 dually reactive samples.

Figure 8:
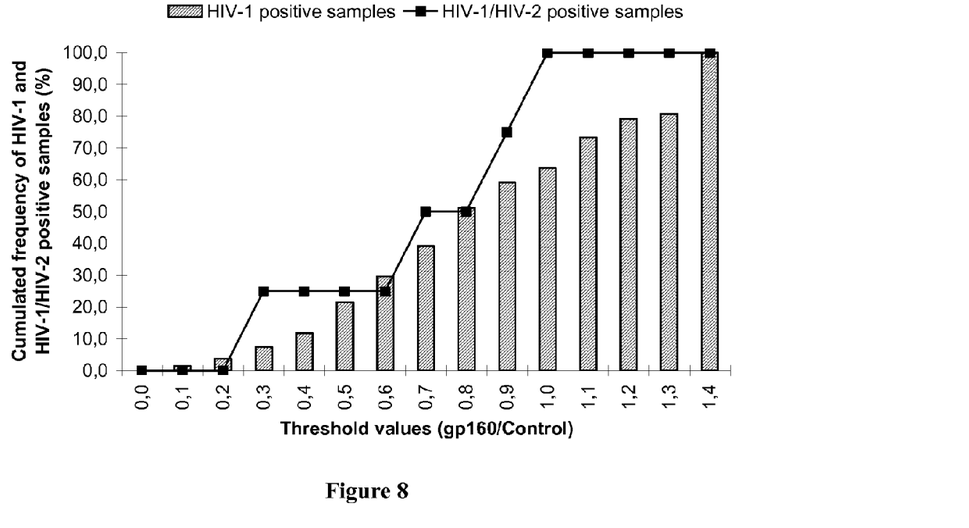
FIG. 8: Cumulated frequencies of HIV-1 positive (n=135) and HIV-1/HIV-2 positive (n=4) samples of lot A according to threshold values for the normalized values for gp160 band intensity (intensity of the gp160 band/intensity of the control band).

The normalized values of the gp160 band intensity (gp160/control) was calculated for each sample using the method as described above. The inventors found that, for this value, the distribution of HIV-1/HIV-2 co-infected samples was similar to that of HIV-1 positive samples (FIG. 8). This value can thus be used to differentiate cross-reactive HIV-2 positive samples from true HIV-1/HIV-2 reactive samples.

Comparison with Multispot HIV-1/HIV-2 Rapid Test

All samples were also tested using the Multispot HIV-1/HIV-2 Rapid Test according to supplier's instructions. Results are presented in Table 1 below.

TABLE 1

Percentage of undifferentiated HIV-2 positive samples in lots A and B

| Lot # | # of HIV-2 positive samples | % undifferentiated HIV-2 positive samples | | | | |
|---|---|---|---|---|---|---|
| | | Multispot neat sample | Geenius without ratio | Multispot diluted sample | Geenius with mean value (a) | Geenius with normalized value (b) |
| A | 154 | 73.4 | 66.9 | 7.1 | 6.5 | 5.8 |
| B | 132 | 78.2 (c) | 68.2 | 1.5 | 4.6 | 7.6 |

(a) Geenius with mean value ((gp160 + 41)/control)/2) (threshold 0.6)
(b) Geenius with normalized value (gp160/control) (threshold 0.3)
(c) Calculated with 55 samples on a total of 132 HIV-2 positive samples This table presents the percentage of undifferentiated HIV-2 positive samples in lots A and B obtained with the Multispot test with and without dilution, the Geenius test without using any ratio for the interpretation (only based on appearance of color on test lines), and the Geenius test using the normalized values for gp160 band (with a threshold of 0.3) or the mean values for gp160 and gp41 bands (with a threshold of 0.6) for differentiate cross-reactive samples from true reactive samples.

These results demonstrate that interpretation of the Geenius test with the ratio (gp16/control) or ((gp160+gp41)/control)/2) allows to reach a lower of undifferentiated HIV reactive samples than the Multispot test with the benefit of no need for diluting samples and thus simplifying the procedure.

Comparison with INNO-LIA™ HIV I/II Score 18 of these HIV-2 positive samples were tested using the INNO-LIA™ HIV I/II Score test, the Geenius test without using any ratio for the interpretation (only based on appearance of color on test lines), and the Geenius test using the mean values for gp160 and gp41 bands (with a threshold of 0.6) or the normalized values for gp160 band (with a threshold of 0.3) for differentiate HIV-1/HIV-2 cross-reactive samples from HIV-2 true reactive samples.

All samples were tested with the INNO-LIA™ HIV I/II Score test according to supplier's instructions.

TABLE 2

HIV-2 positive samples tested using the INNO-LIA ™ HIV I/II Score test and the Geenius test with or without using ratio for interpretation.

| | INNO-LIA ™ HIV I/II Score test | Geenius without ratio | Geenius with mean value (a) | Geenius with normalized value (b) |
|---|---|---|---|---|
| Boca 250 | HIV positive | Probable HIV-2 | Probable HIV-2 | Probable HIV-2 |
| Boca 251 | Probable HIV-2 | Probable HIV-2 | Probable HIV-2 | Probable HIV-2 |
| Boca 252 | Probable HIV-2 | HIV-1/HIV-2 cross-reactivity | Probable HIV-2 | Probable HIV-2 |
| Boca 253 | HIV positive | HIV-1/HIV-2 cross-reactivity | Probable HIV-2 | Probable HIV-2 |
| Boca 254 | Probable HIV-2 | HIV-1/HIV-2 cross-reactivity | Probable HIV-2 | Probable HIV-2 |
| Boca 255 | Probable HIV-2 | Probable HIV-2 | Probable HIV-2 | Probable HIV-2 |
| Boca 256 | Probable HIV-2 | HIV-1/HIV-2 cross-reactivity | Probable HIV-2 | Probable HIV-2 |
| Boca 257 | Probable HIV-2 | HIV-1/HIV-2 cross-reactivity | Probable HIV-2 | Probable HIV-2 |
| Boca 258 | HIV positive | HIV-1/HIV-2 cross-reactivity | Probable HIV-2 | Probable HIV-2 |
| Boca 259 | Probable HIV-2 | HIV-1/HIV-2 cross-reactivity | Probable HIV-2 | Probable HIV-2 |

TABLE 2-continued

HIV-2 positive samples tested using the INNO-LIA ™ HIV I/II Score test and the Geenius test with or without using ratio for interpretation.

| | INNO-LIA ™ HIV I/II Score test | Geenius without ratio | Geenius with mean value (a) | Geenius with normalized value (b) |
|---|---|---|---|---|
| Boca 261 | Probable HIV-2 | HIV-1/HIV-2 cross-reactivity | Probable HIV-2 | Probable HIV-2 |
| Boca 263 | Probable HIV-2 | Probable HIV-2 | Probable HIV-2 | Probable HIV-2 |
| Boca 264 | HIV positive | HIV-1/HIV-2 cross-reactivity | Probable HIV-2 | Probable HIV-2 |
| Boca 265 | HIV positive | HIV-1/HIV-2 cross-reactivity | Probable HIV-2 | Probable HIV-2 |
| Boca 266 | Probable HIV-2 | HIV-1/HIV-2 cross-reactivity | Probable HIV-2 | Probable HIV-2 |
| Boca 267 | Probable HIV-2 | HIV-1/HIV-2 cross-reactivity | Probable HIV-2 | Probable HIV-2 |
| Boca 268 | Probable HIV-2 | Probable HIV-2 | Probable HIV-2 | Probable HIV-2 |
| Boca 269 | Probable HIV-2 | Probable HIV-2 | Probable HIV-2 | Probable HIV-2 |

(a) Geenius with mean value ((gp160 + 41)/control)/2) (threshold 0.6)
(b) Geenius with normalized value (gp160/control) (threshold 0.3)

With the INNO-LIA™ HIV I/II Score test 27.8% of this panel remained undifferentiated.

Using the method of the invention with the Geenius device, the normalized values for gp160 band intensity (gp160/control) and a threshold of 0.3 or the mean values for gp160 and gp41 band intensities [((gp160+gp41)/control)/2)] and a threshold of 0.6, all samples were correctly classified as HIV-2 positive results.

REFERENCES

Arora and Seth, Gene Ther Mol Biol Vol 7, 37-42, 2003
Barin et al., AIDS Res Hum Retroviruses. 1996 Sep. 1; 12(13):1279-89.
Benjouad et al., J Virol. 1993 March; 67(3):1693-7.
Delaney et al., J Clin Virol. 2011 December; 52 Suppl 1:S5-10
Espejo and Uribe, J Clin Microbiol. 1990 September; 28(9): 2107-10
Guyader et al. Nature 326:662-669, 1987
Penn-Nicholson et al., Virology. 2008 Mar. 15; 372(2):442-56.
Ng et al., Anal Bioanal Chem. 2010 June; 397(3):991-1007.
Ntemgwa et al. Antimicrob Agents Chemother 2009; 53(9): 3611-9.
Pandori and Branson, Expert Rev Anti Infect Ther 2010; 8(6):631-3
Robinson et al., J Virol. 1990 November; 64(11):5301-5.
Song et al., Biomed Microdevices. 2012 Feb. 29
Styer et al. J Clin Virol. 2011 December; 52 Suppl 1:S35-40
Tomaras et al., J Virol. 2008 December; 82(24):12449-63
Xu et al., J Virol. 1991 September; 65(9):4832-8.

The invention claimed is:

1. An in vitro method for determining whether a normalized value or a mean value of normalized values for at least one HIV-1 envelope antigen is above or below a predetermined threshold in a fluid sample obtained from a subject who is either HIV-2 positive or HIV-1/HIV-2 positive, the method comprising:
   (a) contacting the fluid sample from the subject with the at least one HIV-1 envelope antigen and a control reagent that can bind human immunoglobulins, wherein said antigen and said control reagent are immobilized on distinct sites on a solid support, for a time and under conditions allowing the formation of complexes between antibodies present in the sample and (i) said at least one HIV-1 envelope antigen and (ii) said control reagent;
   (b) detecting the formation of said complexes using a system generating quantifiable signal;
   (c) dividing the intensity of the signal obtained for said at least one HIV-1 envelope antigen by the intensity of the signal obtained for the control reagent to obtain the normalized value for said at least one HIV-1 envelope antigen;
   (d) if several HIV-1 envelope antigens are used, optionally calculating the mean value of normalized values for HIV-1 envelope antigens; and
   (e) determining whether the normalized value or the mean value of the normalized values of the at least one HIV-1 envelope antigen is above or below the predetermined threshold.

2. The method according to claim 1, wherein said at least one HIV-1 envelope antigen is selected from the group consisting of recombinant gp160, gp41 and gp120, an antigenic fragment thereof, and a peptide comprising an immunodominant epitope of gp160, gp41 or gp120.

3. The method according to claim 1, wherein said at least one HIV-1 envelope antigen is selected from the group consisting of recombinant gp160, an antigenic fragment thereof, or a peptide comprising an immunodominant epitope of gp160.

4. The method according to claim 3, wherein said at least one HIV-1 envelope antigen is recombinant gp160.

5. The method according to claim 3, wherein in step (a) the fluid sample is further contacted with an HIV-1 envelope antigen selected from the group consisting of recombinant gp41, an antigenic fragment thereof, or a peptide comprising an immunodominant epitope of gp41.

6. The method according to claim 5, wherein in step (a) the fluid sample is further contacted with a peptide comprising an immunodominant epitope of gp41.

7. The method according to claim 3, wherein the predetermined threshold for the normalized value for gp160 antigen is about 0.3.

8. The method according to claim 7, wherein the predetermined threshold for the normalized value for gp160 antigen is between 0.27 and 0.33.

9. The method according to claim 5, wherein the predetermined threshold for the mean value for gp160 and gp41 antigens is about 0.6.

10. The method according to claim 9, wherein the predetermined threshold for the mean value for gp160 and gp41 antigens is between 0.54 and 0.66.

11. The method according to claim 1, wherein in step (a) the fluid sample is further contacted with at least one HIV-2 antigen.

12. The method according to claim 11, wherein said at least one HIV-2 antigen is selected from the group consisting of recombinant gp36, gp105 and gp140, an antigenic fragment thereof, and a peptide comprising an immunodominant epitope of gp36, gp105 or gp140.

13. The method according to claim 1, wherein in step (a) the fluid sample is further contacted with at least one HIV-1 core antigen and/or at least one HIV-1 pol antigen.

14. The method according to claim 1, wherein in step (a) the fluid sample is further contacted with at least one HIV-1 antigen selected from the group consisting of recombinant p31 and p24, an antigenic fragment thereof, and a peptide comprising an immunodominant epitope of p31 or p24.

15. The method according to claim 1, wherein the fluid sample is selected from the group consisting of whole blood, serum and plasma.

16. The method according to claim 1, wherein the immunoassay is a migration type assay, a flow-through test, a dipstick assay or a microfluidic assay.

17. The method according to claim 16, wherein the immunoassay is a migration type assay.

18. The method according to claim 1, wherein the control reagent is selected from the group consisting of protein A, protein G, protein A/G, protein L and derivatives thereof, and an anti-human immunoglobulin antibody.

19. The method according to claim 18, wherein the control reagent is protein A.

20. The method according to claim 1, wherein in step (b) the system generating quantifiable signal is a reagent binding to human immunoglobulins, and wherein the reagent is conjugated with a detectable label.

21. The method according to claim 20, wherein the reagent binding to human immunoglobulins is selected from the group consisting of protein A, protein G, protein A/G, protein L and derivatives thereof, and an anti-human immunoglobulin antibody.

22. The method according to claim 21, wherein the reagent binding to human immunoglobulins is protein A.

23. The method according to claim 20, wherein the detectable label is selected from the group consisting of colloidal metals; non-metallic colloids; carbon; visible, fluorescent, luminescent and chemiluminescent dyes; magnetic particles; radioactive elements; and enzymes.

24. The method according to claim 1, wherein the system generating quantifiable signal is a conjugate comprising a protein selected from the group consisting of protein A, protein G, protein A/G, protein L and derivatives thereof, coupled with a colloidal metal or a fluorescent, luminescent or chemiluminescent dye.

25. The method according to claim 1, wherein the system generating quantifiable signal is protein A conjugated with colloidal gold.

26. The method according to claim 1, wherein the normalized level of only the at least one HIV-1 envelope antigen is determined to be above or below the predetermined threshold.

* * * * *